United States Patent [19]

Mahood

[11] Patent Number: 5,559,167
[45] Date of Patent: Sep. 24, 1996

[54] GAMMA IRRADIATED THERMOPLASTICS AND ARTICLES

[75] Inventor: James A. Mahood, Morgantown, W. Va.

[73] Assignee: General Electric Company, Pittsfield, Mass.

[21] Appl. No.: 361,785

[22] Filed: Dec. 21, 1994

Related U.S. Application Data

[63] Continuation-in-part of Ser. No. 307,545, Sep. 16, 1994, Pat. No. 5,424,348, which is a continuation-in-part of Ser. No. 096,530, Jul. 22, 1993, abandoned.

[51] Int. Cl.$^6$ .................................................. C08K 5/529
[52] U.S. Cl. ............................................. 523/136; 524/117
[58] Field of Search ............................ 524/117; 523/136

[56] References Cited

U.S. PATENT DOCUMENTS

| | | |
|---|---|---|
| 3,039,993 | 6/1962 | Friedman . |
| 3,056,823 | 10/1962 | Hechenbleikner et al. . |
| 3,264,247 | 8/1966 | Friedman . |
| 3,281,381 | 10/1966 | Hechenbleikner et al. . |
| 3,305,520 | 2/1967 | Fritz et al. . |
| 3,305,526 | 2/1967 | Guttag . |
| 3,342,767 | 9/1967 | Buckley . |
| 3,415,906 | 12/1968 | Shepard et al. . |
| 3,437,720 | 4/1969 | Guttag . |
| 3,441,633 | 4/1969 | Friedman . |
| 3,467,733 | 9/1969 | Dever et al. . |
| 3,482,002 | 12/1969 | Dever et al. . |
| 3,483,147 | 12/1969 | Friedman . |
| 3,488,407 | 1/1970 | Schall . |
| 3,509,091 | 4/1970 | Cleveland et al. . |
| 3,558,554 | 1/1971 | Kuriyama et al. . |
| 3,646,173 | 2/1972 | Gordon et al. . |
| 3,714,302 | 1/1973 | Dever et al. . |
| 3,794,629 | 2/1974 | Eimers et al. . |
| 3,845,168 | 10/1974 | Guttag . |
| 4,036,719 | 7/1977 | Lyons . |
| 4,086,304 | 4/1978 | Hutton et al. . |
| 4,196,117 | 4/1980 | Spivack . |
| 4,318,845 | 3/1982 | Spivack et al. . |
| 4,405,739 | 9/1983 | Kinson . |
| 4,507,415 | 3/1985 | Kasai et al. . |
| 4,529,533 | 7/1985 | Chasar . |
| 4,666,959 | 5/1987 | Weissberger et al. . |
| 4,708,979 | 11/1987 | Pedrazzetti et al. . |
| 4,755,546 | 7/1988 | Hechenbleikner et al. . |
| 4,782,170 | 11/1988 | Bae et al. . |
| 4,797,438 | 1/1989 | Kletecka et al. . |
| 4,882,374 | 11/1989 | Wang et al. . |
| 4,888,369 | 12/1989 | Moore, Jr. . |
| 4,912,155 | 3/1990 | Burton . |
| 4,956,406 | 9/1990 | Myers et al. . |
| 4,957,954 | 9/1990 | Iizuka et al. . |
| 5,015,526 | 5/1991 | Kubo et al . |
| 5,023,285 | 6/1991 | Horn . |

FOREIGN PATENT DOCUMENTS

| | | |
|---|---|---|
| 0559461A1 | 9/1993 | European Pat. Off. . |
| 0635514A1 | 1/1995 | European Pat. Off. . |
| 2944254 | 5/1980 | Germany . |
| 2087399 | 5/1982 | United Kingdom . |
| 2093463 | 9/1982 | United Kingdom . |

OTHER PUBLICATIONS

Phosphorus and Sulfer, 1983, vol. 15, pp. 9–13.

*Primary Examiner*—Veronica P. Hoke

[57] ABSTRACT

Thermoplastic compositions are stabilized with a phosphite of the formula:

$$H_3C-CH_2-CH_2-CH \diagdown \qquad CH_2-O \diagdown$$
$$\qquad\qquad\qquad\qquad C \qquad\qquad P-O-\!\!\!\bigcirc\!\!\!-Y^2$$
$$CH_3-CH_2 \diagup \qquad CH_2-O \diagup$$
$$\qquad\qquad\qquad\qquad\qquad\qquad\qquad\qquad Y^1$$

with $C(CH_3)_3$ substituent on the ring.

wherein $Y^1$ is an alkyl and $Y^2$ is selected from tert-butyl and sec-butyl. The phosphite is particularly effective for thermoplastics irradiated with high energy gamma-radiation. Irradiated articles made with the phosphite stabilized thermoplastic compositions exhibit improved discoloration resistance compared to various other phosphite stabilized thermoplastic compositions.

16 Claims, No Drawings

GAMMA IRRADIATED THERMOPLASTICS AND ARTICLES

This is a continuation-in-part of application Ser. No. 08/307,545 filed on Sep. 16, 1994, now U.S. Pat. No. 5,424,348 which is a continuation of Ser. No. 96,530, Jul. 22, 1993, now abandoned.

BACKGROUND OF THE INVENTION

Field of the Invention

The present invention relates to gamma irradiated thermoplastics and gamma irradiated thermoplastic articles, and more particularly relates to gamma irradiated thermoplastic compositions containing a phosphite and gamma irradiated articles made from a thermoplastic composition containing a phosphite.

DESCRIPTION OF THE RELATED ART

Thermoplastic compositions are useful as materials for making laboratory ware and disposable medical articles, see Kletecka et al., U.S. Pat. No. 4,797,438, issued Jan. 10, 1989, which is incorporated herein by reference, and include articles such as trays, funnels, Petridishes, blow-molded IV bottles, hypodermic syringes, needle shields, and surgical gowns. Sterilization of the thermoplastics and articles can be achieved by exposure to gamma radiation having an energy level of from 0.5 to 10 megarads for a period of time, for example, 1 minute to 24 hours.

Exposure of various thermoplastics to gamma radiation can result in the undesirable formation of color and a degradation in physical properties.

Accordingly, it is desired to provide thermoplastic compositions and articles which exhibit enhanced levels of resistance to color formation and degradation upon exposure to sterilizing amounts of gamma radiation.

SUMMARY OF THE PRESENT INVENTION

The present invention involves a thermoplastic composition containing a neoalkyl phosphite of the formula:

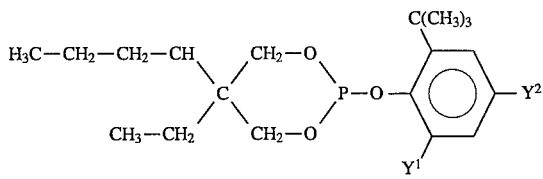

wherein $Y^1$ is an alkyl and $Y^2$ is selected from tert-butyl and sec-butyl, articles made therefrom, gamma irradiated thermoplastic compositions containing the phosphite, and gamma irradiated articles made from the compositions. The articles and compositions exhibit reduced levels of color formation and degradation compared to articles and compositions utilizing various other phosphites.

DETAILED DESCRIPTION OF THE INVENTION

The polymeric compositions contain a resin, preferably a thermoplastic resin and a phosphite of the formula:

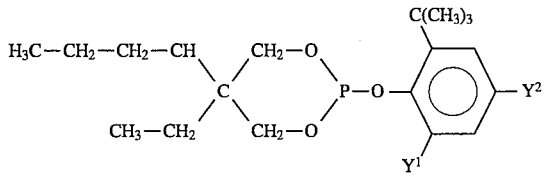

wherein $Y^1$ is an alkyl and $Y^2$ is selected from tert-butyl and sec-butyl. The thermoplastic resin is preferably present at a level of from 50 to 99.9 weight percent based on the total weight of the composition, more preferably from 90 to 99.5 weight percent thereof, and most preferably from 95 to 99 weight percent thereof. The phosphite is preferably present at a level of from 0.01 to 5 weight percent based on the total weight of the composition, more preferably from 0.015 to 0.5 percent by weight thereof, and most preferably from 0.02 to 0.2 percent by weight thereof. The thermoplastic resin is preferably an olefin polymer, and is more preferably a polypropylene polymer.

The olefin polymers contemplated herein include homopolymers and copolymers of monoolefins, preferably those monoolefins containing 1–4 carbon atoms. Illustrative examples include polyethylene (including low density, high density, ultra high molecular weight and linear low density polyethylene), polypropylene, EPDM polymers, ethylene-propylene copolymers and polyisobutylene. The stabilization of mixtures of any of these olefin polymers and copolymers likewise is contemplated.

The present invention involves a neoalkyl aryl phosphite of the formula:

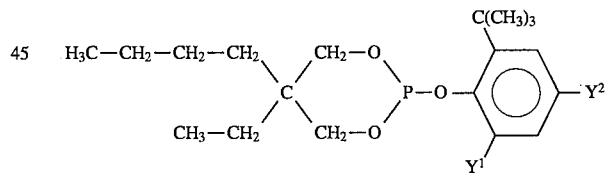

wherein $Y^1$ is independently selected from the group consisting of alkyl radicals, and preferably $Y^1$ is a tert-butyl group and $Y^2$ is a tert-butyl or sec-butyl group.

The phosphite may be made by the reaction of 2-ethyl-2-butyl-1,3-propane diol with $PCl_3$ in the absence of a catalyst, HCl acceptor and solvent to produce an intermediate product of the formula:

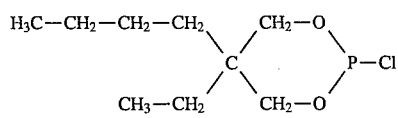

followed by the reaction with a hydroxyaryl compound of the formula:

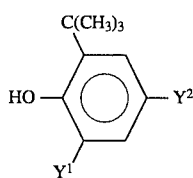

wherein $Y^1$ and $Y^2$ are as defined above. Suitable reaction methods are set out in Great Britain Patent 2087399A, Spivak et al. U.S. Pat. No. 4318845 issued 1982, and Article in Phosphourous & Sulfur Journal by J. D. Spivak et al. 1983, vol. 15, pp. 9–13, all of which are incorporated herein by reference.

The reaction between the diol and $PCl_3$ may be conducted in known manner, as by mixing the reactants together at room temperature, or preferably, by cooling the $PCl_3$ to a temperature between 5–15 degrees centigrade prior to addition of diol to the reactor. An excess of either reactant may be employed although it is preferred to operate with substantially stoichiometric amounts of the diol and $PCl_3$. The reaction temperature is preferably maintained between 5–15 degrees centigrade. This temperature may be readily controlled by regulating the rate of diol addition. The esterification reaction is quite exothermic in the absence of a solvent, but a temperature moderating effect is produced by the cooling effect of vigorous HCl evolution. Hence, by effective control of diol addition, the reaction may be made self-regulating in the temperature range between 5–15 degrees centigrade.

After the reaction has gone to completion, the bulk of the by-product HCl may optionally be removed by gently raising the temperature of the product to about 50 degrees centigrade and applying a vacuum.

The reaction between the intermediate product of the reaction discussed in the preceding paragraph and hydroxyaryl compound may be conducted in the same reaction vessel that was employed to produce the crude intermediate by merely introducing the hydroxyaryl compound into the reactor.

The reaction between the hydroxyaryl compound and the intermediate product in some instances may be carried out at a temperature between 35 to 100 degrees centigrade and preferably between about 45 to about 80 degrees centigrade. The pressure of the reaction system is maintained between about 50 millimeters mercury absolute to atmospheric pressure. The reaction reaches substantial completion in from 1 to about 8 hours and for practical purposes it is preferably operated under temperature and pressure conditions which will afford the maximum amount of product within 3 to about 5 hours. Although a stoichiometric excess of either reactant may be employed, it is preferred to operate with substantially stoichiometric quantities.

The hydroxyaryl compound may be any compound of the formula:

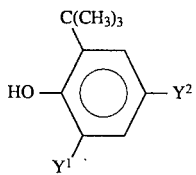

in which $Y^1$ is selected from the group consisting of alkyl groups preferably having from 1 to 8 carbon atoms, more preferably methyl or t-butyl. The reaction can be completed in the presence of a base such as an amine acceptor. Since $Y^1$ is an alkyl group, an amine acceptor should be added to help drive this reaction. If $Y^1$ is a tert-alkyl group, such as t-butyl, then a stociometric amount of amine acceptor should be present. $Y^2$ is selected from sec-butyl and t-butyl groups. If $Y^2$ is a t-butyl group then the phosphite is a solid at room temperature.

After completion or near completion of the reaction, HCl generated during the process may readily be substantially removed by evacuating the reactor vessel. No special precautions need to be taken to remove all the HCl present, as by addition of HCl acceptor or via controlled neutralization of the acidity. The product may then be recovered by distillation, or crystallization.

The phosphites have $Y^1$ as an alkyl group such as methyl or t-butyl in order to inhibit ultraviolet light yellowing of the phosphite. If $Y^1$ is hydrogen the phosphite will have sensitivity to UV yellowing. The preferred phosphite has a phenolic degradation product boiling point of greater than 250° C., more preferably greater than 260° C. so that the volatility of the degradation product during processing of the stabilized polymer, such as polyolefins such as polypropylene which processes at 240° C. and above, is minimized. The problem of excessive volatiles can be minimized by employing an 2,4-di-butyl-6-alkyl phenyl group because such groups have corresponding 2,4-di-butyl- 6-alkyl phenol degradation products which have a boiling point of greater than 260° C.

The present invention also is a stabilized polymer composition which includes an effective amount of one or more of the phosphites described above. An amount of the phosphites of the invention is considered to be an "effective amount" when the polymer composition containing the phosphites of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more.

The thermoplastic resins may be selected from various polymers as set out below. Polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain (or be free of) various conventional additives, such as the following:

1. Antioxidants 1.1 Alkylated monophenols, for example: 2,6-di-tertbutyl- 4-methylphenol, 2-tert-butyl-4,6-dimethylphenol, 2,6-di-tert-butyl-4-ethylphenol, 2,6-di-tert-butyl- 4-n-butylphenol, 2,6-di-tert-butyl-4-isobutylphenol, 2,6-dicyclopentyl-4-methylphenol, 2-(alpha-methylcyclohexyl)- 4,6 dimethylphenol, 2,6-di-octadecyl- 4-methylphenol, 2,4,6,-tricyclohexyphenol, 2,6-di-tert-butyl-4-methoxymethylphenol.

1.2 Alkylated hydroquinones, for example, 2,6-di-tert-butyl- 4-methoxyphenol, 2,5-di-tert-butylhydroquinone, 2,5-di-tert-amyl-hydroquinone, 2,6-diphenyl- 4octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl- 3-methylphenol), 4,4'-thio-bis-(6-tert-butyl-2-methylphenol).

1.4 Alkylidene-bisphenols, for example, 2,2'-methylene-bis-( 6-tert-butyl-4-methylphenol), 2,2'-methylene-bis-(6-tert-butyl-4-ethylphenol), 2,2'-methylene-bis-( 4-methyl-6-(alphamethylcyclohexyl(phenol), 2,2'-methylene-bis-(4-methyl- 6-cyclohexylphenol), 2,2'-methylene-bis-(6-nonyl-4-methylphenol), 2,2'-methylene-bis-(6-nonyl-4-methylphenol), 2,2'-methylene-bis-(6-(alpha-methylbenzyl)- 4-nonylphenol), 2,2'-methylene-bis-(6-(alpha,alpha-dimethylbenzyl)- 4-nonyl-phenol). 2,2'-methylene-bis-( 4,6-di-tert-butylphenol), 2,2'-ethylidene-bis-( 6-tert-butyl-4-isobutylphenol), 4,4'-methylene-bis-( 2,6-di-tert-butylphenol), 4,4'-methylene-bis-( 6-tert-butyl-2-methylphenol), 1,1-bis (5-tert-butyl-4-hydroxy-2-methylphenol)butane, 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy- 2-methylphenyl)-3-dodecyl-mercaptobutane, ethyleneglycol-bis-(3,3,-bis-(3'-tert-butyl-4'-hydroxyphenyl)-butyrate)-di-( 3-tert-butyl-4-hydroxy- 5-methylphenyl)-dicyclopentadiene, di-(2-(3'-tert-butyl- 2'hydroxy-5'methyl-benzyl)-6-tert-butyl-4-methylphenyl)terephthalate.

1.5 Benzyl compounds, for example, 1,3,5-tris-( 3,5-di-tert-butyl-4-hydroxybenzyl)-2,4,6-trimethylbenzene, bis-(3, 5-di-tert-butyl-4-hydroxybenzyl)sulfide, isooctyl 3,5-di-tert-butyl-4-hydroxybenzyl-mercapto-acetate, bis-(4-tert-butyl-3-hydroxy- 2,6-dimethylbenzyl)dithiol-terephthalate. 1,3,5-tris-(3,5-di-tert-butyl-4-hydroxybenzyl)isocyanurate. 1,3,5-tris-(4-tert-butyl- 3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl- 4-hydroxybenzylphosphonate, 1,3,5-tris-(3,5-dicyclohexyl- 4-hydroxybenzyl)isocyanurate.

1.6 Acylaminophenols, for example, 4-hydroxylauric acid anilide, 4-hydroxy-stearic acid amilide, 2,4-bis-octylmercapto-6-(3,5-tert-butyl-4-hydroxyanilino)-s-triazine, octyl-N-(3,5-di-tert-butyl- 4-hydroxyphenyl)-carbamate.

1.7 Esters of beta-(3,5-di-tert-butyl-4-hydroxyphenyl)-propionic acid with monohydric or polyhydric alcohols, for example, methanol, diethyleneglycol, octadecanol, triethyleneglycol, 1,6-hexanediol, penta-erythritol, neopentylglycol, tris-hydroxyethylisocyanurate, thiodiethyleneglycol, dihydroxyethyl oxalic acid diamide.

1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy-3-methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4-hydroxyphenol)-propionic acid for example, N,N'-di( 3,5-di-tert-butyl-4-hydroxyphenylpropionyl)-hexamethylen-diamine, N,N'-di-(3,5-di-tert-butyl-4-hydroxyphenylpropionyl) trimethylenediamine, N,N'-di- (3,5-di-tert-butyl-4-hydroxyphenylpropionyl)hydrazine.

2. UV absorbers and light stabilizers.

2.1 2-(2'-hydroxyphenyl)-benzotriazoles, for example, the 5'methyl-,3'5'-di-tert-butyl-,5'-tert-butyl-, 5'(1,1,3,3-tetramethylbutyl)-,5-chloro-3',5'-di-tert-butyl-, 5-chloro-3'tert-butyl-5'methyl-,3'sec-butyl- 5'tert-butyl-,4'-octoxy,3',5'-ditertamyl 3',5'-bis-(alpha, alpha-dimethylbenzyl)-derivatives.

2.2 2-Hydroxy-benzophenones, for example, the 4-hydroxy-4-methoxy-,4-octoxy,4-decloxy-,4-dodecyloxy-, 4-benzyloxy,4,2',4'-trihydroxy-and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)resorcinol, benzoylresorcinol, 2,4-di-tert-butylphenyl- 3,5-di-tert-butyl-4-hydroxybenzoate and hexadecyl-3,5-di-tert-butyl-4-hydroxybenzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)- 2-methylindoline.

2.5 Nickel compounds, for example, nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-1auroyl-5-hydroxy-pyrazole, optionally with additional ligands.

2.6 Sterically hindered amines, for example bis(2,2,6,6-tetramethylpiperidyl)-sebacate, bis-( 1,2,2,6,6-pentamethylpiperidyl)-sebacate, n-butyl 3,5-di-tert-butyl-4-hydroxybenzyl malonic acid bis (1,2,2,6,6,-pentamethylpiperidyl)ester, condensation product of 1-hydroxyethyl-2,2,6,6-tetramethyl- 4-hydroxy-piperidine and succinic acid, condensation product of N,N'-(2,2,6,6-tetramethylpiperidyl)-hexamethylendiamine and4-tert-octylamino- 2,6-dichloro-1,3,5-s-triazine, tris-( 2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis( 3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-( 3,5-di-tert-butyl-4-hydroxy hydrocinnamoyloxy)piperdine; and N-(1-hydroxy-2,2,6,6-tetramethyl-piperidin- 4-yl)-epsiloncaprolactam.

2.7 Oxalic acid diamides, for examples, 4,4'-dioctyloxy-oxanilide, 2,2'-di-octyloxy-5',5'-di-tertbutyloxanilide, 2,2'-di-dodecyloxy-5',5'di-tert-butyl-oxanilide, 2-ethoxy-2'-ethyl-oxanilide, N,N'bis( 3-dimethylaminopropyl)-oxalamide, 2-ethoxy-5-tert-butyl- 2'-ethyloxanilide and its mixture with 2-ethoxy- 2'ethyl-5,4-di-tert-butyloxanilide and mixtures of ortho-and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)hydrazine, salicyloylamino-1,2,4-triazole, bis-benzyliden-oxalic acid dihydrazide.

4. Additional phosphites and phosphonites, for example, triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tertbutylphenyl)pentaerythritol diphosphite tristearyl sorbitol triphosphite, and tetrakis(2,4-di-tertbutylphenyl) 4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmitate, antimony pyrocatecholate or zinc pyrocatecholate.

8. Nucleating agents, for example, 4-tert butylbenzoic acid, adipic acid, diphenylacetic acid.

9. Fillers and reinforcing agents, for example, calcium-carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N,N-dibenzylaminoxy)propanoate;ethyl-3-(N,N-dibenzylaminoxy)propanonoate; 1,6-hexamethylenebis(3-N,N-dibenzylaminoxy)proponoate); methyl-(2-(methyl)- 3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)propanoate; 3-(N,N-dibenzylaminoxy)propanoic acid potassium salt; and 1,6-hexamethylene bis(3-(N-allyl-N-dodecyl aminoxy)propanoate).

11. Other additives, for example, plasticizers, epoxidized vegetable oils such as epoxidized soybean oils, lubricants, emulsifiers, pigments, hydroxylamines such as R₂NOH wherein R is a $C_1$ to $C_{30}$ alkyl group such as propyl or stearyl, optical brighteners, flameproofing agents, anti-static agents, blowing agents and thiosynergists such as dilaurythiodipropionateordistearylthiodipropionate. Optionally, the polymer compositions are free of the above additives.

Olefin polymers may be produced by polymerization of olefins in the presence of Ziegler-Natta catalysts optionally on supports such as but not limited to Mg $Cl_2$, chromium salts and complexes thereof, optionally supported on Silica or other materials. They may also be produced utilizing catalysts based on cyclopentadiene complexes of metals typically complexes of Ti and Zr.

It is also believed the present method would be useful for thermoset polymer compositions containing a thermoset resin such polyester thermosets, allyls, acrylics, epoxies, urethanes, silicones, phenolics, bismaleimides, alkyd, ureas, melamines, and furans.

Articles of sterilizable polymer most likely to benefit from sterilization by gamma-radiation, are the components of hypodermic syringes, catheters, prosthetic devices, and self-supporting polymer films from about 0.5 mil to about 2 mil thick used for packaging, and for making colostomy bags, and devices for coping with incontinence or posturinary drip.

A sterilizing amount of gamma irradiation usually involves a dosage of from 0.5 to 7 megarads accumulated over a period of from 1 minute to 24 hours.

The radiation employed to achieve sterilization of the particular object is ionizing radiation, usually gamma radiation produced from a cobalt-60 or cesium-137 radioactive nuclei. A second type of radiation, electron beam radiation, is also suitable for sterilization. Electron beam radiation is produced in a high voltage electron acceleration.

Enhanced resistance to degradation usually involves enhanced retention of physical properties such as impact strength and, percent elongation and yield strength.

Enhanced resistance to color formation usually involves reduced levels of increase in yellowness index as measured by ASTM test D-1225.

TABLE 1

| Ex | ADD | YI Chance |
|---|---|---|
| A | I | 8.65 |
| B | Phos-B | 8.05 |
| 1 | Phos 1 | 5.2 |
| C | I/Phos B | 33.7 |
| D | I/Phos D | 38.2 |
| E | I/Phos E | 15.2 |
| 2 | I/Phos 2 | 9.7 |
| 3 | I/Phos 1 | 8.7 |

Examples A–E are comparative examples. Examples 1–3 are examples of the present invention. Examples A–E and 1–3 used a base formulation of Profax 6301 brand polypropylene with 500 ppm (weight basis) of Calcium stearate and 500 ppm of the respective additive(s) listed I is a hindered phenolic commercially available as Irganox 1010.

Phos B is bis (2,4-di-t-butylphenyl) pentaerythritol diphosphite.

Phos 1 is of the formula

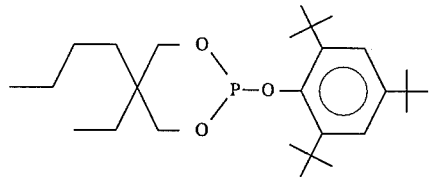

Phos D is tris(2,4-di-tert-butylphenyl) phosphite.

Phos E is Tetrakis(2,4-di-tert-butylphenyl)4,4'biphenylylenediphosphonite.

Phos 2 is of the formula

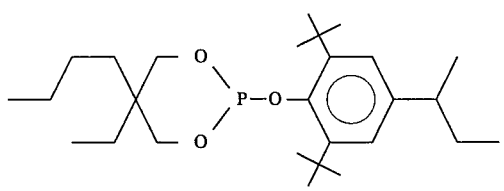

Note the relatively small yellowness index (YI) change of example 1 compared to comparative examples A and B; and note the relatively small yellowness index change of examples 2 and 3 compared to comparative examples C–E. All examples (A–E and 1–3) yellowness index changes were the result of exposure to 5M rads of gamma irradiation.

What is claimed is:

1. A method for enhancing resistance to discoloration incurred by gamma irradiation of an article made from a polymeric resin composition, said composition comprising a polymeric resin, said method comprising:
   (a) incorporating into said composition prior to gamma irradiation a phosphite at a level of from 0.01 to 5 percent by weight based on the total weight of the composition, said phosphite being of the formula:

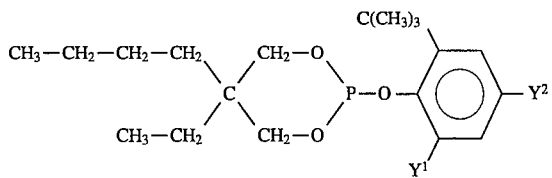

wherein $Y^1$ is alkyl and $Y^2$ is tert-butyl or sec-butyl; and (b) then subjecting said article to gamma irradiation.

2. The method of claim 1, wherein the resin is a polyolefin resin.

3. The method of claim 1 wherein $Y^1$ is tert-butyl.

4. The method of claim 1 wherein $Y^1$ is methyl.

5. The method of claim 1 wherein the total dosage of said gamma radiation is from 0.5 to 5.0 megarads accumulated over a period of from 1 to 24 hours.

6. A method for sterilizing a shaped article made from a thermoplastic resin composition, said composition comprising a thermoplastic resin, said method comprising:
   (a) incorporating into said composition a phosphite of the formula:

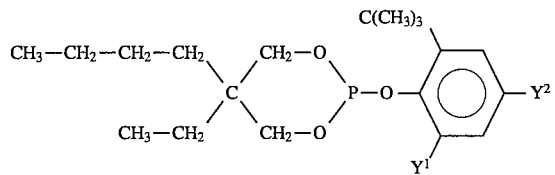

wherein $Y^1$ is alkyl and $Y^2$ is tert-butyl or sec-butyl; and (b) exposing said article to gamma radiation in an amount sufficient to sterilize the article.

7. The method of claim 6 wherein the amount of gamma radiation is from 0.5 to 10.0 megarads accumulated over a period of from 1 minute to 24 hours.

8. The method of claim 6, wherein the thermoplastic resin is a polyolefin resin.

9. The method of claim 6, wherein the thermoplastic resin is a polypropylene resin.

10. The method of claim 6 wherein $Y^1$ is tert-butyl.

11. The method of claim 6 wherein $Y^1$ is methyl.

12. A gamma irradiated medical article made from a thermoplastic resin composition, said composition comprising a thermoplastic resin and a gamma radiation stabilizing amount of a phosphite of the formula:

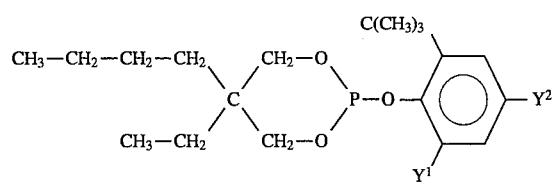

wherein $Y^1$ is alkyl and $Y^2$ is tert-butyl or sec-butyl and said article having been subjected to a sterilizing amount of gamma radiation.

13. The article of claim 12, wherein the thermoplastic resin is a polyolefin resin.

14. The article of claim 12, wherein the thermoplastic resin is a polypropylene resin.

15. The article of claim 12 wherein $Y^1$ is tert butyl.

16. The article of claim 12, wherein said composition consists essentially of said phosphite and said thermoplastic resin.

* * * * *